United States Patent [19]

Ehrenfreund

[11] 4,164,403

[45] Aug. 14, 1979

[54] METHOD FOR INHIBITING PLANT GROWTH

[75] Inventor: Josef Ehrenfreund, Allschwil, Switzerland

[73] Assignee: Ciba-Geigy Corporation, Ardsley, N.Y.

[21] Appl. No.: 912,916

[22] Filed: Jun. 6, 1978

[30] Foreign Application Priority Data

Jun. 9, 1976 [CH] Switzerland .......................... 7252/76
Jun. 10, 1977 [CH] Switzerland .......................... 7172/77

[51] Int. Cl.$^2$ .............................................. A01N 5/00
[52] U.S. Cl. ............................................ 71/76; 71/113
[58] Field of Search ................................... 71/113, 76

[56] References Cited

U.S. PATENT DOCUMENTS

| | | | |
|---|---|---|---|
| 3,859,171 | 1/1975 | Demny et al. ..................... | 195/96 |
| 3,869,277 | 3/1975 | Berger et al. ..................... | 71/113 |
| 3,923,491 | 12/1975 | O'Brien et al. ..................... | 71/76 |
| 4,014,898 | 3/1977 | Keith et al. ..................... | 71/113 |

OTHER PUBLICATIONS

Collogues Internation AUX C.N.R.S., 1975, p. 161.

*Primary Examiner*—Catherine L. Mills
*Attorney, Agent, or Firm*—Harry Falber

[57] ABSTRACT

The present invention concerns a method for inhibiting plant growth, especially of grasses, cereals and soya by treating the emerged plants with an effective amount of a compound of the formula

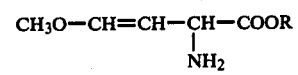

or of a salt thereof. Preferred are salts of the L-trans-form of the said compound.

4 Claims, No Drawings

METHOD FOR INHIBITING PLANT GROWTH

The present invention relates to a method and a composition for inhibiting plant growth using an unsaturated amino acid derivative as active substance.

The production of the antibiotically active substance, L-2-amino-4-methoxy-trans-3-butenoic acid (AMB), by fermentation from a fungus is described in U.S. Pat. No. 3,859,171. This substance, as well as the salts thereof with bases, possesses antibacterial and antitrichomonal properties and can be used as a pharmaceutical.

On the other hand, the 4-[2'-aminoethoxy] derivative of this 2-amino-3-butenoic acid (and salts thereof) is known e.g. from U.S. Pat. Nos. 3,775,255 and 3,869,277 and German Offenlegungsschrift No. 2,327,639; and the corresponding saturated amino acid, α-amino--(2-aminoethoxy)-butyric acid, is also known from U.S. Pat. No. 3,865,694, and has been proposed as a fruit abscission agent on account of its ability to promote ethylene formation in plants (German Offenlegungsschrift No. 2,461,138). However, precisely the opposite property as an inhibitor of ethylene formation is ascribed to this compound in U.S. Pat. No. 3,887,615. L-2-amino-2-methoxy-trans-3-butenoic acid also possesses the same inhibitory action (Colloques internationaux C.N.R.S., 1975, page 161).

The above mentioned analogue, 2-amino-4-(2'-aminoethoxy)-3-butenoic acid, possesses antibiotic, especially antimicrobial, antiprotozoal and antihelmintic activity (U.S. Pat. No. 3,775,255). Herbicidal properties of this compound have also been described (German Offenlegungsschrift No. 2,327,639).

The constitution and synthesis of related compounds and intermediates thereof are also dealt with in Tetrahedron Letters 31, 2629–2636 (1975).

It has now surprisingly been found that the different isomers of the known 2-amino-4-methoxy-3-butenoic acid (ABM) and its salts possess excellent plant growth inhibiting properties, which make them suitable for use as growth inhibitors, ripening retarders etc.

The method of the present invention for inhibiting plant growth comprises treating emergent plants with an effective amount of a composition which contains, as active substance, a compound of the formula I

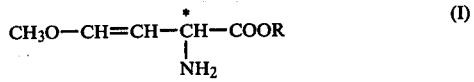

wherein R represents hydrogen or the equivalent of a cation of an inorganic or organic base, including quaternary nitrogen bases.

Because of the olefinic double bond, the compounds of the formula I exist in cis- and trans-isomeric forms, and on account of the asymmetric carbon atom C*, each of these isomeric forms can occur in the optically active D- and L-form, and can also be obtained as any mixture of these optical isomers and as racemate (DL).

The plant growth inhibiting composition of the present invention contains, as active component, a 2-amino-4-methoxy-3-butenoic acid, or a salt thereof, of the formula I, in addition to carriers and/or other solid or liquid adjuvants.

The free acid (R=H), the cation $H^{\oplus}$ of which can form with the amino group a zwitter ion $NH_3^{\oplus}H^{\ominus}$, is preferred, as well as the alkali metal and alkaline earth metal salts thereof, the salts of protonated and quaternary nitrogen bases, such as $HN^{\oplus}(CH_2-CH_2-OH)$, $H^{\oplus} NH_2-C_{12}H_{25}$ etc. Salts of strong acids having a pK<5 are also useful active substances.

Among the geometrical isomers, the trans-form is preferred on account of its action. With the resulting D- and L-forms it cannot be definitely stated at present whether a clear preference of the L-forms over the D-forms may be assumed.

According to the present invention, both the trans- and cis-forms as well as the pure optical isomers and mixtures thereof in any reciprocal ratio are to be understood as active substances of the composition.

Suitable cations R are in principle all those which are capable of salt formation and are tolerated by plant physiology, that is to say, also those which themselves possess growth inhibiting properties. The ionic counter-ions of the ammonium salts must also be tolerated by plants and can themselves inhibit growth.

By plant growth inhibiting properties is meant all control of natural plant development which effects a retardation of this process. Particular mention is to be made of the inhibition of the vegetative plant growth of monocotyledonous and dicotyledonous plants, especially in grass (lawns), cereal crops, soya, ornamentals etc. It is also possible to bring about artificially retarding effects in plant development (sucker formation, blossoming, fruit setting, fruit ripening, fruit drop etc.). The time of application of the composition of the present invention depends on the development stage of the plants to be treated and on the object of the treatment, for example on the condition of the plant in respect of blossoming, fruit formation etc., and is thus to be determined correctly in each individual case. The active substances of the formula I can be applied before or after the emergence of the plants, for example to the seeds or seedlings, to roots, tubers, stems, leaves, blossoms or other parts of plants, for example, by applying the active substance itself in the form of a composition to the plants and/or by treating the nutrient medium of the plant (soil).

The primary effect attained by the compounds of the formula I consists in the desired reduction of the plant size, in particular of the growth in height. In general, a certain change in the form of the plant is allied to this reduction in size. As a direct consequence of the reduction of the growth in height the plant is strengthened: leaves and stems are better developed. By shortening the distances between internodes in monocotyledonous plants the breaking strength is increased. In this way it is possible to prevent to a great extent harvest losses caused by thunderstorms, prolonged rainfall etc., which usually result in a lodging of cereals. As side-effect, the reduced growth in height of useful plants results in a substantial saving in the use of fertilisers. This also applies equally to ornamental plants and ornamental grass plots, turf for sporting activities, or other grass-covered open spaces.

A much greater problem posed by pure grass cultivations, however, is the actual cutting of the grass itself, whether in open spaces of urban areas, industrial sites, playing fields, along main roads, on railway embankments or the embankments of water bodies. In all these cases it is necessary to cut the turf or grass periodically. This operation is not only time-consuming, complicated and expensive in respect of labour and machinery, but involves the personnel concerned and traffic users in considerable hazard.

For this reason there is an urgent need in areas with extensive traffic networks to maintain and tend the grassy covering for strengthening road shoulders and embankments on traffic routes on the one hand, and on the other to keep it at a reasonable height by simple means during the entire vegetation period. This need is fulfilled in a very advantageous manner by applying the composition of the invention.

The active substances of the present invention thus intervene in the physiological processes of plant growth and are therefore growth regulators which have a growth retarding effect.

The different inhibiting effects depend substantially on the time of application, referred to the development stage of the plant, and on the concentrations employed. Accordingly, growth inhibitors can also bring about that the nutrients are beneficial to the flower and fruit formation, whereas the vegetative growth is restricted.

Further effects of the growth inhibitors of the formula I are:

delaying flower formation and fruit setting; retarding the ripening and change in colour of harvested fruit or fruit still on the plant, which is important especially when dispatching harvested fruit over long distances; delaying and inhibiting undesired premature fruit and leaf drop (antiethylene action); inhibition of sucker formation (suckers in tobacco plants); maintaining the dormant state of plants, thereby promoting frost resistence in early spring; preventing resin flow in stone fruit trees; inhibiting tuber formation and germination of seeds, etc.

The active substances of the formula I (acids and salts) are known.

The production of L-trans-2-amino-4-methoxy-3-butenoic acid by fermentation is described in U.S. Pat. No. 3,859,171.

The synthesis of 2-amino-4-methoxy-3-butenoic acid is described in the following Example.

MANUFACTURING EXAMPLE 15 g of the compound (L-form)

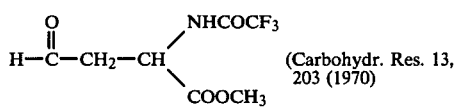

(Carbohydr. Res. 13, 203 (1970))

are boiled for 4 hours in 50 ml of methanol with the addition of 0.5 g of ammonium chloride and 20 ml of trimethyl orthoformate. Distillation of the reaction product yields 13 g (73% of theory) of the compound

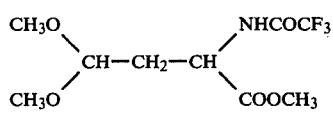

as a colourless oil with a boiling point of 120° C./0.1 torr.

4 parts by weight of the above compound, dissolved in dichlorobenzene, are kept for several hours at 170° C. with the addition of 0.1 part by weight of o-nitrobenzoic acid, in the course of which methanol is split off. After removal of the solvent, chromatography on silica gel yields 1 part by weight of the compound

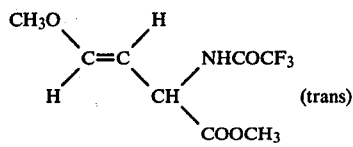

with a melting point of 61°–62° C.

Finally, 2 parts by weight of this compound are treated with 100 parts by volume of a 0.4 normal Ba(OH)$_2$ solution and the mixture is left to stand overnight. The barium ions are then precipitated by the addition of excess triethylammonium hydrogen carbonate and the resulting trans-2-amino-4-methoxy-3-butenoic acid of the formula

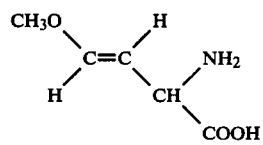

is purified by chromatography on cellulose. The yield is 0.76 part by weight or 70% of theory. Melting point >235° C. (decomp.).

The final product was not optically pure and, in addition to substantial amount of the L-form, contained also amounts of the D-form. The cis-form can be prepared in similar manner.

The compositions of the present invention are prepared in a manner known per se by intimately mixing and grinding active substances of the general formula I with suitable solid or liquid carriers and adjuvants customarily used in the art of formulation, for example natural or regenerated mineral substances, solvents, dispersants, wetting agents, tackifiers, thickeners and binders.

The compositions of the invention can be processed to:

Solid formulations dusts, tracking powders, granules, (coated granules, impregnated granules and homogeneous granules).

Liquid formulations (a) active substance concentrates which are dispersible in water: wettable powders, pastes, emulsions, emulsifiable concentrates;
(b) solutions.

Solid forms (dusts, tracking powders), are obtained by mixing the active substances with solid carriers. Suitable carriers are, for example: kaolin, talc, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder residues of plant extractions, activated charcoal etc. These substances can either be used singly or in admixture with one another.

Granulates can be prepared by dissolving the active substances in an organic solvent and applying the resultant solution to a granulated material, for example attapulgite, SiO₂, granicalcium, bentonite etc., and then evaporating the solvent.

Polymer granulates can also be prepared by impregnating a finished, porous polymer granulate (urea/formaldehyde polymers, polyacrylonitrile, polyester and others), which has a specific surface area and a favourable predetermined adsorption/desorption ratio, with the active substances, for example in the form of their solutions (in a low boiling solvent) and removing the solvent. Polymer granulates of this kind in the form of microgranules having a bulk density of 300 g/liter to 600 g/liter can also be produced with the aid of atomisers. The dusting can be carried out from aircraft over extensive areas of cultures of useful plants.

It is also possible to obtain granulates by compacting the carrier with the active substance and carriers and subsequently comminuting the product.

To these mixtures can also be added additives which stabilize the active substance and/or nonionics, anionics and cationics, which, for example, improve the adhesion of the active ingredients on plants or parts of plants (tackifiers and agglutinants) and/or ensure a better wettability (wetting agents) and dispersibility (dispersing agents). Examples of suitable substances are: olein/-chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl moiety, lignin sulphonic acids, the alkali metal and alkaline earth metal salts thereof, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of urea and formaldehyde, and also latex products.

Water-dispersible concentrates, i.e. wettable powders, pastes and emulsifiable concentrates, are compositions which can be diluted with water to the desired concentration. They consist of active substance, carrier, optionally additives which stabilize the active substance, surface-active substances and anti-foam agents and, if appropriate, solvents.

Wettable powders and pastes are obtained by mixing and grinding the active substances with dispersing agents and pulverulant carriers in suitable devices until homogeneity is attained. Suitable carriers are, for example, those already mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of napthalene or naphthalene sulphonic acids with phenol and formaldehyde, as well as alkali metal, ammonium and alkaline earth metal salts of lignin sulphonic acid, in addition, alkylarysulphonates, alkali metal and alkaline earth metal salts of dibutynaphthalenesulphonic acid, fatty alcohol sulphates, such as salts of sulphated hexadecanols, heptadecanols, octadecanols, and salts of sulphated fatty alcohol glycol ethers, the sodium salt of oleyl methyl tauride, ditertiary ethylene glycols, dialkyldilaurylammonium chloride and fatty acid alkali metal and alkaline earth metal salts.

Suitable anti-foam agents are silicone oils.

The active substance is so mixed, ground sieved and strained with the additives mentioned above that, in wettable powders, the solid particle size of 0.02 to 0.04 mm and in pastes, of 0.03 mm, is not exceeded. Emulsifiable concentrates and pastes are manufactured by using dispersing agents, such as those cited previously above, organic solvents, and water. Examples of suitable solvents are: alcohols, benzene, xylenes, toluene, dimethyl sulphoxide, and mineral oil fractions which boil between 120° and 350° C. The solvents must be practically odourless, not phytotoxic, and inert to the active substances.

Furthermore, the compositions of the invention can be applied in the form of solutions. For this purpose the active substances or several active substances of the general formula I are dissolved in suitable organic solvents, mixtures of solvents or in water. Aliphatic and aromatic hydrocarbons, chlorinated derivatives thereof, alkylnaphthalenes and mineral oils, singly or in admixture, can be used as organic solvents.

The above described compositions contain between 0.1 and 95%, preferably between 1 and 80%, of active substance. Formulations can be diluted to a concentration as low as 0.001%. The rates of application are normally from 0.1 to 10 kg of active substance per hectare, preferably 0.25 to 5 kg per hectare. The active substances of the formula I can be formulated for example as follows. The parts denote parts by weight.

Dusts

The following substances are used to obtain (a) a 5% and (b) a 2% dust:

(a)

5 parts of active substance,
95 parts of talc;

(b)

2 parts of active substance,
1 part of highly disperse silicic acid,
97 parts of talc.

The active substances are mixed with the carriers and ground.

Granules

The following substances are used to produce 5% granules:

5 parts of active substance,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with epichlorohydrin and the mixture is dissolved in 6 parts of acetone. The polyethylene glycol and cetyl polyglycol ether are then added. The resultant solution is sprayed on kaolin, and the acetone is subsequently evaporated in vacuo.

Wettable powder

The following constituents are used for the preparation of (a) a 40%, (b) and (c) a 25%, and (d) a 10% wettable powder:

(a)

40 parts of active substance,
5 parts of sodium ligninsulphonate,
1 part of sodium dibutylnaphthalenesulphonate,
54 parts of silicic acid;

(b)

25 parts of active substance,
4.5 parts of calcium ligninsulphonate, 1.9 parts of Champagne chalk-hydroxyethyl cellulose mixture (1:1),
1.5 parts of sodium dibutylnaphthalenesulphonate,
19.5 parts of silicic acid,
19.5 parts of Champagne chalk,
28.1 parts of kaolin;

(c)

25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselguhr,
46 parts of kaolin;

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed in suitable mixers with the additives, and the mixture is then ground in appropriate mills and rollers to yield wettable powders which can be diluted with water to give suspensions of the desired concentration. Such suspensions are very suitable for treating plants to influence growth and development.

Emulsifiable concentrate

The following substances are used to produce a 25% emulsifiable concentrate:
25 parts of active substance,
2.5 parts of epoxidised vegetable oil,
10 parts of an alkylarylsulphonate/fatty alcohol polyglycol ether mixture,
5 parts of dimethyl formamide,
57.5 parts of xylene.

By diluting such a concentrate with water it is possible to manufacture emulsions of the desired concentration which are suitable for application to plants for inhibiting growth.

To determine the growth inhibiting action, tests were carried out with grasses, cereals, soya and save. The test method for determining the growth inhibition of grasses was carried out as follows: Each of the grass species *Lolium perenne, Dactylis glomerata, Festuca ovina, Poa pratensis* Cynodon, was reared separately from seeds in a plastic dish measuring $9 \times 15 \times 7.5$ cm in an earth-/turf/sand mixture (6:3:1) and cut back each week to a height of 4 cm. One day after the last cutting (40 days after sowing), the active substances were applied as a spray mixture in an amount of 25 ml per 4 dishes. The rate of application was 5 kg/ha and 2.5 kg/ha (or 700 liters and 350 liters respectively per hectare).

The first evaluation was made 10 days and the second 21 days after application. The rating 9 denotes no inhibition of growth (as untreated control), and the rating 1 denotes strong inhibition (no further growth). Strong growth inhibition of all the above species of grass was determined with the active substance trans-2-amino-4-methoxy-3-butenoic acid of the present invention (ratings 1 and 2 in both concentrations).

Similar tests with this active substance also showed a marked growth inhibition of cereals (Triticum, Hordeum, Secale), soya and save (ratings 1 to 4, depending on the concentration.

What is claimed is:

1. A method for inhibiting vegetative plant growth which comprises treating emerged plants with a non-phytotoxic effective amount of an active substance of the formula I

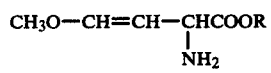

wherein R represents hydrogen or a plant physiologically acceptable salt thereof.

2. The method according to claim 1 wherein the active substance used is trans-2-amino-4-methoxy-3-butenoic acid or a plant physiologically acceptable salt thereof.

3. The method according to claim 1 wherein the treated plants are grasses, cereals and soya.

4. The method according to claim 2 wherein the active substance used is the optical L-form of trans-2-amino-4-methoxy-3-butenoic acid or a plant physiologically acceptable salt thereof.

* * * * *